United States Patent [19]
Maxson et al.

[11] Patent Number: 4,900,734
[45] Date of Patent: Feb. 13, 1990

[54] NOVEL PHARMACEUTICAL COMPOSITION CONTAINING ESTRADIOL AND PROGESTERONE FOR ORAL ADMINISTRATION

[76] Inventors: Wayne S. Maxson, 11181 NW 26th Dr., Coral Springs, Fla. 33065; Joel T. Hargrove, 820 Hatcher La.; Joe H. Delk, 103 Cayce Valley Dr., both of Columbia, Tenn. 38401

[21] Appl. No.: 90,095

[22] Filed: Aug. 27, 1987

[51] Int. Cl.$^4$ .............................................. A61K 31/56
[52] U.S. Cl. ................................... 514/171; 514/177; 514/182; 514/899
[58] Field of Search ............... 514/899, 951, 960, 177, 514/170, 182, 935, 171

[56] References Cited

U.S. PATENT DOCUMENTS

| | | |
|---|---|---|
| 2,675,342 | 4/1954 | Lee et al. |
| 3,733,407 | 5/1973 | Segre ................................... 514/177 |
| 3,755,575 | 8/1973 | Lerner |
| 4,150,128 | 4/1979 | Jasionowski ........................ 514/177 |
| 4,196,188 | 4/1980 | Besins |
| 4,425,339 | 1/1984 | Pitchford ............................ 514/170 |

FOREIGN PATENT DOCUMENTS

| | | | |
|---|---|---|---|
| 0136011 | 4/1985 | European Pat. Off. ............ | 514/177 |
| 0918219 | 2/1965 | France ................................ | 514/177 |
| 0258110 | 12/1985 | Japan ................................... | 514/177 |
| 0549118 | 6/1977 | U.S.S.R. ............................. | 514/170 |
| 0686736 | 9/1979 | U.S.S.R. ............................. | 514/170 |
| 0475936 | 11/1937 | United Kingdom ................ | 514/177 |

OTHER PUBLICATIONS

Hargrove et al., "Absorption of Oral Progesterone Is Inhibited by Vehicle and Physical Characteristics", Abstract of 32nd Annual Meeting, Soc. Gyn. Invest. (3/85).
Swern, "Bailey's Ind. Oil & Fat Products", 3d ed. (Interscience, NY, 1965), pp. 207-212, 222 & 224-226.
Mattsson et al., "Evaluation of Continuous Oestroge--Progesteren Regime for Climacteric Complants", Maturitas, 4:95-102 (1982).
de Lignieres et al., "Differential Effects of Exogenous Oestradiol and Progesterone on Mood in Post--Menopausal Women", Maturitas, 4:67 (1982).
Staland, "Continuous Treatment with Natural Oestrogens and Progestogens, A Method to Avoid Endometrial Simulation", Maturitas 3:145-156 (1981).
Riis et al., "Post-Menopausal Bone Loss: Effects of Oestrogens and Progestogens, A Review", Maturitas, 8:267-274 (1986).
Judd, H. L., Cleary, R. E., Creasman, W. T., Figge, D. C., Kase, N., Rosewaks, Z., Tagatz, G.E., Estrogen Replacement Therapy, Obstet Gynecol, 1981;58:267-275.
Hammond, C. B., Maxson W. S., Current Status of Estrogen Therapy for Menopause, Fertil Steril, 1982;37:5-25.
Henderson, B. E., Ross, R. K., Paganini-Hill, A., Mack, T. M., Estrogen Use and Cardiovascular Disease, Am J Obstet Gynecol, 1986;154:1181-1186.
Henderson, B. E., Paganini-Hill, A., Ross, R. K., Estrogen Replacement Therapy and Protection from Acute Myocardial Infarction, Am J Obstet Gynecol, 1988;159:312-317.

(List continued on next page.)

Primary Examiner—H. M. S. Sneed
Assistant Examiner—James Saba
Attorney, Agent, or Firm—Bacon & Thomas

[57] ABSTRACT

A pharmaceutical composition is provided for oral administration. The composition comprises estradiol dissolved in an oil vehicle containing a suspension of micronized progesterone. The oil vehicle is high in glycerides of polyunsaturated fatty acids. The estradiol and micronized progesterone contained in the oil are more readily absorbable in the blood stream and achieve enhanced estradiol and progesterone blood serum levels. The pharmaceutical composition according to the invention can be readily formulated into capsules and administered for the treatment of menopausal symptoms.

34 Claims, 7 Drawing Sheets

OTHER PUBLICATIONS

Smith, D. C., Prentice, R., Thompson, D. J., Herrmann, W. L., Association of Exogenous Estrogen and Endometrial Carcinoma, N Engl J Med, 1975;293:1164–1167.

Ziel, H. K., Finkle, W. D,. Increased Risk of Endometrial Carcinoma Among Users of Conjugated Estrogens, N Engl J Med, 1975;293:1167–1170.

Whitehead, M, Lane, G, Siddle, N, Townsend, P, King, R., Avoidance of Endometrial Hyperstimulation in Estrogen-Treated Postmenopausal Women, Seminars in Reproductive Endocrinology, 1983;1:41–53.

Gambrell, R. D., Jr., Bagnell, C. A., Greenblatt, R. B., Role of Estrogens and Progesterone in the Etiology and Prevention of Endometrial Cancer: Review, Am J Obstet Gynecol, 1983;146:696–707.

Gambrell, R. D., Jr., Massey, F. M., Castaneda, T. A., Ugenas, A. J., Ricci, C. A., Wright, J. M., Use of the Progestogen Challenge Test to Reduce the Risk of Endometrial Cancer, Obstet Gynecol, 1980;55:732–738.

Holst, J., Cajander, S., von Schoultz, B., Endometrial Effects of a Continuous Percutaneous Oestrogen/Low Dose Progestogen Regimen for Climateric Complaints, Maturitas, 1987;9:63–67.

Lind, T., Cameron, E. C., Hunter, W. M., Leon, C., Moran, P. F., Oxley, A., Gerrard, J., Lind, U. C. G., A Prospective, Controlled Trial of Six Forms of Hormone Replacement Therapy Given to Postmenopausal Women, Br J Obstet Gynaecol, 1979;86(Suppl. 3):1–29.

Magos, A. L., Brincat, M., Studd, J. W. W., Wardle, P., Schlesinger, P., O'Dowd, T., Amenorrhea and Endometrial Atrophy with Continuous Oral Estrogen and Progestogen Therapy in Postmenopausal Women, Obstet Gynecol, 1985;65:496–499.

Staland, B., Continuous Treatment with Natural Oestrogens and Progestogens, A Method to Avoid Endometrial Stimulation, Maturitas, 1981;3:145–156.

Mattsson, L. A., Cullberg, G., Samsioe, G., Evaluation of a Continuous Oestrogen-Progestogen Regimen for Climacteric Complaints, Maturitas, 1982;4:95–102.

Mattsson, L. A., Cullberg, G., Samsioe, G., A Continuous Estrogen-Progestogen Regimen for Climacteric Complaints Effects on Lipid and Lipoprotein Metabolism, Acta Obstet Gynecol Scand, 1984;63:673–677.

Hellberg, D, Nilsson, S., Pilot Study to Evaluate a New Regimen to Treat Climacteric Complaints with Cyclic Combined Oestradiol Valerate/Medroxyprogesterone Acetate, Maturitas, 1987;9:103–107.

Weinstein, L., Efficacy of a Continuous Estrogen-Progestin Regimen in the Menopausal Patient, Obstet Gynecol, 1987;69:929–932.

Prough, S. G., Aksel, S., Wiebe, R. H., Shepherd, J., Continuous Estrogen/Progestin Therapy in Menopause, Am J Obstet Gynecol, 1987;157:1449–1453.

Luciano, A. A., Turksoy, R. N., Carleo, J., Hendrix, J. W., Clinical and Metabolic Responses of Menopausal Women to Sequential Versus Continuous Estrogen and Progestin Replacement Therapy, Obstet Gynecol, 1988;71:39–43.

Mashchak, C. A., Lobo, R. A., Dozono-Takano, R., Eggena, P., Nakamura, R. M., Brenner, P. F., Mishell, D. R., Comparison of Pharmacodynamic Properties of Various Estrogen Formulations, Am J Obstet Gynecol, 1982;144:511–518.

Gorrill, M. J., Marshall, J. R., Pharmacology of Estrogens and Estrogen-Induced Effects on Nonreproductive Organs and Systems, J Reprod Med Suppl, 1986;31:842–847.

Ottosson, U. B., Oral Progesterone and Estrogen/Progestogen Therapy, Effects of Natural and Synthetic Hormones on Subfractions of HDL Cholesterol and Liver Proteins, Acta Obstet Gynecol Scand [Suppl], 1984;127:1–37.

Fahraeus, L., Larsson-Cohn, U., Wallentin, L.. L—Norgestrel and Progesterone Have Different Influences on Plasma Lipoproteins, Europ J Clin Invest, 1983;13:447–453.

Fahraeus, L., Metabolic Consequences of Postmenopausal Estrogen and Progestogen Treatment, Acta Obstet Gynecol Scand Suppl, 1985;132:19–21.

Hirvonen, E., Malkonen, M., Manninen, V., Effects of Different Progestogens on Lipoproteins during Postmenopausal Replacement Therapy, N Eng J Med, 1981;304:560–563.

Larsson-Cohn, U., Fahraeus, L., Wallentin, L., Goran, Z., Lipoprotein Changes May Be Minimized by Proper Conmposition of a Combined Oral Contraceptive, Fertil Steril, 1981;35:172–179.

Padwick, M. L., Endacott, S. R. N., Whitehead, MI., Efficacy, Acceptability, and Metabolic Effects of (List continued on next page.)

OTHER PUBLICATIONS

Transdermal Estradiol in the Management of Postmenopausal Women, Am J Obstet Gynecol, 1985;152:1085–1091.

Powers, M. S., Schenkel, L., Darley, P. E., Good, W. R., Balestra, J. C., Place, V. A., Pharmacokinetics and Pharmacodynamics of Transdermal Dosage forms of 17B-Estradiol: Comparison with Conventional Oral Estrogens Used for Hormone Replacement, Am J Obstet Gynecol, 1985;152:1099–1106.

De Lignieres, B., Basdevant, A., Thomas, G., Thalabard, J. C., Mercier Bodard, C., Conard, J., Guyene, T. T., Mairon, N., Corvol, P., Guy Grand, B. et al., Biological Effects of Estradiol-17 beta in Postmenopausal Women: Oral Versus Percutaneous Administration, J Clin Endocrinol Metab, 1986; 62:536–541.

Stanczyk, F. Z., Shoupe, D., Nunez, V., Macias-Gonzales, P., Vijod, M. A., Lobo, R. A., A Randomized Comparison of Nonoral Estradiol Delivery in Postmenopausal Women, Am J Obstet Gynecol, 1988;159:1540–1546.

Rock, J. A., Wentz, A. C., Cole, K. A., Kimball, Jr,. A. W., Zacur, H. A., Early, S. A., Jones, G. S., Fetal Malformations Following Progesterone Therapy During Pregnancy: A Preliminary Report, Fertil Steril, 1985;44:17–19.

Wentz, A. C., Assessment of Estrogen and Progestin Therapy in Gynecology and Obstetrics, Clin Obstet Gynecol, 1977;20:461–482.

Arafat, E. S., Hargrove, J. T., Maxson, W. S., Desiderio, D. M., Wentz, A. C., Andersen, R. N., Sedative and Hypnotic Effects of Oral Administration of Micronized Progesterone May Be Mediated through Its Metabolites, Am J Obstet Gynecol, 1988;159:1203–1209.

Hargrove, J. T., Maxson, W. S., Wentz, A. C., Burnett, L. S., Menopausal Hormone Replacement Therapy with Continuous Oral Micronized Estradiol and Progesterone, Obstet Gynecol, 1989; (In Press).

Nichols, K. C., Schenkel, L., Benson, H., 17 beta-Estradiol for Postmenopausal Estrogen Replacement Therapy, Obstet Gynecol Surv, 1984;39:230–245.

Jensen, J., Riis, B. J., Strom, V., Nilas, L., Christiansen, C., Long-Term Effects of Percutaneous Estrogens and Oral Progesterone on Serum Lipoproteins in Postmenopausal Women, Am J Obstet Gynecol, 1987;156:66–71.

Ottosson, U. B., Johansson, B. G., von Schoultz, B., Subfractions of High-Density Lipoprotein Cholesterol During Estrogen Replacement Therapy: A Comparison Between Progestogens and Natural Progesterone, Am J Obstet Gynecol ,1985;151:746–750.

Whitehead, M. I., Townsend, P. T., Gill, D. K., Collins, W. P., Campbell, S., Absorption and Metabolism of Oral Progesterone, Br Med J, 1980;280:825–827.

Maxson, W. S., Hargrove, J. T., Bioavailability of Oral Micronized Progesterone, Fertil Steril, 1985;44:622–626.

ACOG Technical Bulletin, Estrogen Replacement Therapy, ACOG 1986; No. 93–Apr.:1–6.

Judd, H., Utian, W. H., Introduction: What We Hope to Learn, Am J Obstet Gynecol, 1987;156:1279–1280.

NOVEL PHARMACEUTICAL COMPOSITION CONTAINING ESTRADIOL AND PROGESTERONE FOR ORAL ADMINISTRATION

FIELD OF THE INVENTION

The present invention relates to a pharmaceutical composition containing estradiol and progesterone as the active ingredients. The pharmaceutical composition according to this invention is useful for the combined administration of these steroids for replacement hormone therapy in the treatment of menopausal woman.

BACKGROUND OF THE INVENTION

Esterodiol is a naturally occurring steroidal sex hormone known as 17 beta-estradiol or 1,3,5(10)estratriene-3,17 beta-estradiol. It has the chemical formula:

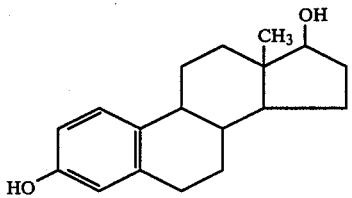

Progesterone is naturally occurring steroidal sex hormone also known as pregn-4-ene-3,20 dione. It has the chemical formula:

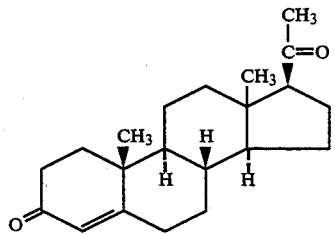

Estradiol is the predominant estrogen hormone produced by the human ovaries during the first half or follicular phase of the menstral cycle. Estradiol is also the principal hormone which maintains bone density, reduces vasomotor symptoms, and maintains the normal structure of the female genital organs following menopause.

Progesterone is the principal hormone of the second half, or luteal phase of the menstral cycle. Among other functions, progesterone acts as an estrogen antagonist. For example, it is well known that prolonged administration of estrogen can result in endometrial hyperplasia and even uterine cancer, whereas progesterone appears to block this unwanted effect of the endometrium.

It is desirable to use estrodiol and/or progesterone to treat a variety of endocrinol disorders, and also for use as a contraceptive. However, it is well known that neither of these compounds are suitable for oral administration due to the manner in which they are absorbed from the digestive system. In particular, these steroidal hormones are carried by the portal system to the liver, where they are rapidly metabolized into inactive metabolites. Consequently, effective oral administration has required excessively high dosage levels to compensate for the metabolic breakdown of these compounds.

In the past, different approaches have been developed to avoid these problems. One approach involves the development of numerous steroidal derivatives which can be orally administered without the objectionable metabolic destruction, and thus they can be orally administered at relatively low dosage levels. For example, estrogenic compounds such as 17 alpha-ethynyl estradiol has been developed for enhanced oral activity. Likewise, progesterone derivatives such as megastrol acetate (6-methyl-17 beta-acetoxy-4,6-pregnadiene-3,20-dione), norethindrone (17 alpha-ethynyl-17-hydroxy-4-estren-3-one), norethynodrel and norethindrone have been prepared to enhance their oral activity. Various estrodiol and progesterone derivatives having enhanced oral activity are disclosed in U.S. Pat. Nos. 3,836,651; 3,755,575, and 3,568,828.

While chemical modifications have resulted in enhanced oral activity of these steroidal hormones, they have also resulted in undesirable side effects. In particular, the synthetic progestins are well known for their side effects, which include masculinization and adverse effects on cholesterol levels, triglyceride levels, and high density lipoprotein levels. In addition, synthetic progestins may also cause fluid retention and depression as significant side effects in contrast to natural progesterone.

A second approach has involved injectionable formulations containing progesterone or estradiol in their natural form. Obviously, daily injection of progesterone or estradiol has many disadvantages, such as pain and discomfort, necessity of maintaining sterility of the drug and hypodermic syringe, and frequent need for professional help in giving the injection.

A third approach has involved development of formulations containing estradiol or progesterone which can be orally administered. One such formulation is an orally active progesterone composition described in U.S. Pat. No. 3,284,303. The oral activity is attributed to the presence of glycerylmonostearate in the composition containing progesterone.

Another formulation is described by Rudel in U.S. Pat. No. 3,828,106. The formulation described by Rudel is said to result in enhanced oral activity of estradiol or progesterone. The oral activity is attributed to the presence of steroidal lipids into the composition. In particular, bile acids and sterols are said to be useful for enhancing the oral activity of these steroidal hormones. It is also stated by Rudel that the steroid-glyceride compositions known in the prior art, such as the ones described in U.S. Pat. 3,284,303, are not suitable due to hydrolysis of the glyceride in the intestine. Thus, it is concluded by Rudel that glyceride and triglyceride carriers, especially when used as a solvent for steroidal hormones, are to be avoided due to hydrolysis in the intestine.

In Patent No. 3,862,311, an orally active progesterone formulation is disclosed. The formulation comprises progesterone, a carrier, and a surfactant. The carrier is preferably polyethylene glycol and the surfactant is an anionic or non-ionic surfactant.

An orally active progesterone has been disclosed in Besins in U.S. Pat. No. 4,196,188. The composition described by Besins contains micronized progesterone suspended in oil for improved oral absorption. The progesterone is in the form of particles in which at least 80% of the particles are between 1–15 mm. However, Besins stresses that particle size of less than 5 mm should be avoided in order to maintain stability for longer than 3 months. Thus, the composition disclosed by Besins has a short shelf life when particle sizes of 1-5 mm are used.

An orally active form of estradiol has been developed by Mead-Johnson and sold under the name "Estrace". Estrace achieves its oral activity by administering the estradiol in the form of micronized particles.

More recently, in an application filed on Apr. 14, 1986, entitled "Pharmaceutical Composition Containing Progesterone"; Ser. No. 850,181; a composition containing miscronized progesterone in an unsaturated oil carrier was described. The composition described in the above-reference application is orally active and is said to be useful for treating pre-menstral symptoms. This composition is lacking in estradiol, which is necessary for hormonal replacement therapy in treating menopausal women. Furthermore, although the above-referenced application provides for enhanced oral activity for progesterone, it provides no information for achieving enhanced oral absorption for estradiol in combination with the progesterone.

Although it is well known to combine synthetic estrogens and progestin compounds in a single formulation, nobody has ever formulated a safe and effective orally active formulation containing estradiol and progesterone in a single dosage unit. Others have failed in meeting this objective, even though the advantages of a single pill or capsule containing both estrogen and a progestin have long been known. The most widely used oral contraceptives contain this combination of synthetic steroids. Recently, Whitehead and Colleagues (Seminars in Reproductive Endocrinology 1: 1 1983) and Magos and Colleagues (Obstet Gynecol 65: 496, 1985) reported on the use of both an estrogen (the non-human, equine, conjugated estrogen) and in a separate preparation, a synthetic progestin or natural progesterone as effective in preventing withdrawal bleeding and endometrial hypolasia in post-menopausal women.

It has also been long recognized that the equine estrogens and the other synthetic estrogens and progestins have both physiologic and non-psychologic properties. The equine estrogens contain a number of estrogen compounds (such as equilin and equilin-sulfate) which are not normally synthesized in the human. These long acting estrogens have the disadvantage of having an unknown effect on the human system.

Customary usage of estrogen and progestin for treating menopause has involved either sequential administration or continuous daily administration of separate estrogen and progestin pills or capsules. These methods of administration have been poorly tolerated for two reasons. First, the sequential administration often results in withdrawl uterine bleeding seen by the patient as a menstral period. This is not well tolerated by older women, and this bleeding often results in the discontinuation of estrogen therapy. Consequently, patients are forced to suffer with their menopausal symptoms. Additionally, discontinuation of estrogen therapy will often times result in persistant monthly withdrawal bleeding.

The disadvantage of the continuous daily preparation is that there is no single pill or capsule available except for the oral contraceptive preparations which can be taken every day in a convenient fashion and minimize the risk of withdrawal bleeding. The synthetic oral contraceptives are currently relatively contra-indicated after age 35 and are rarely prescribed after age 40, because of well known side effects of these synthetic preparations and doses.

With the advancing age of the American population, management of menopause becomes increasingly important to the practicing gynocologist. This importance will soon be amplified by the entry of the baby-boom generation into their climacteric years. In order to optimize the health of this expanding group of women, it becomes imperative that we develop menopausal hormone replacement programs that are safe, effective, and acceptable to them.

Estrogen replacement therapy is known to be effective in relieving menopausal symptoms and genital atrophy. It is useful in the prevention of osteroporosis and its sequelae. The dilemma of endometrial hyperplasia and carcinoma is, to a large extent, obviated by the addition of cyclic progestin as a part of the estrogen replacement program. However, the addition of synthetic progestin induces withdrawal bleeding, and many women find this unacceptable. Recently, continuous estrogen and progestin have been reported to eliminate uterine bleeding, yet maintain the benefits of estrogen replacement therapy. However, the safety of chronic administration of synthetic progestin has been questioned because of its adverse effects on lipids. In addition, many patients experience anonying side effects from synthetic progestin.

Therefore, there is a long felt need to provide a safe and effective hormone therapy drug for treating menopause which avoids the side effect problems associated with the synthetic estrogen and progestin drugs. In addition, effective treatment of menopause requires a formulation which can be conveniently taken every day for a long period of time and which minimizes the risk of withdrawal bleeding and adverse effects on the serum lipids. Also, there is a need for enhancing the absorption or oral activity of 17 beta-estradiol and progesterone so that higher serum levels of the active drug can be more easily and more quickly obtained.

SUMMARY OF THE INVENTION

It is an object of the present invention to provide an orally administratable form of 17 -beta-estradiol and progesterone in a single dosage unit having high oral activity as reflected by peak serum levels of 17 beta-estradiol and progesterone achieved following oral administration of the capsule containing both of these drugs.

It is also an object of this invention to provide a method of hormone replacement therapy for treating menopausal women while avoiding withdrawal bleeding.

It is also an object of this invention to provide a formulation for treating menopausal women on a long-term basis while avoiding adverse effects on the endometrium, chlolesterol levels, triglyceride levels, HDL cholesterol levels, blood pressure and breasts.

It is also an object of this invention to provide adequate serum levels of 17 beta-estradiol and progesterone for treating menopausal women while minimizing the required dosage level necessary to achieve the adequate serum levels.

These and other objects of the invention are achieved by providing a pharmaceutical composition containing micronized progesterone suspended in a highly unsaturated oil carrier containing dissolved estradiol therein. The composition is made by dissolving 17 beta-estradiol in the oil and then suspending crystalline micronized progesterone in the estradiol-oil solution with partial dissolution of the progesterone therein.

The highly unsaturated oil is high in unsaturated and polyunsaturated components. The oil contains mainly glycerides of fatty acids. At least 51% by weight of these glycerides are glycerides of polyunsaturated fatty acids, particularly dienoic acids such as linoleic acid.

The composition is formulated for oral administration, preferably in the form of a dosage unit such as a capsule. Each dosage unit preferably contains 0.2–0.5 mg of estradiol and 50–100 mg of progesterone. Most preferably, capsules are provided containing 3.5 mg of estradiol, and 100 mg of progesterone. The preferred oil is safflower oil.

The method of treating menopausal women comprises administering the above composition to women having menopausal symptoms. Women who have been treated with the composition of this invention are relieved of symptoms without any adverse side effects. In particular, women who are treated with the composition of this invention do not experience withdrawal bleeding of any of the side effects observed with conventional therapy techniques.

Furthermore, the estradiol component of the composition in the form of dissolved 17 beta-estradiol in a highly unsaturated oil such as safflower oil results in enhanced oral activity over the orally active micronized "Estrace" form of estrodiol. This enhanced oil activity is unexpected because the prior art estradiol compositions taught against the use of glyceride oils as a vehicle or, as in the case of "Estrace" required it to be in micronized form. Also, as a result of the combination of estradiol with progesterone, an improvement over compositions containing only micronized progesterone in a oil is realized, since the combination results in an enhanced orally active drug for treating menopause without withdrawal bleeding or other adverse side effects.

DETAILED DESCRIPTION OF THE INVENTION

Figure 1:
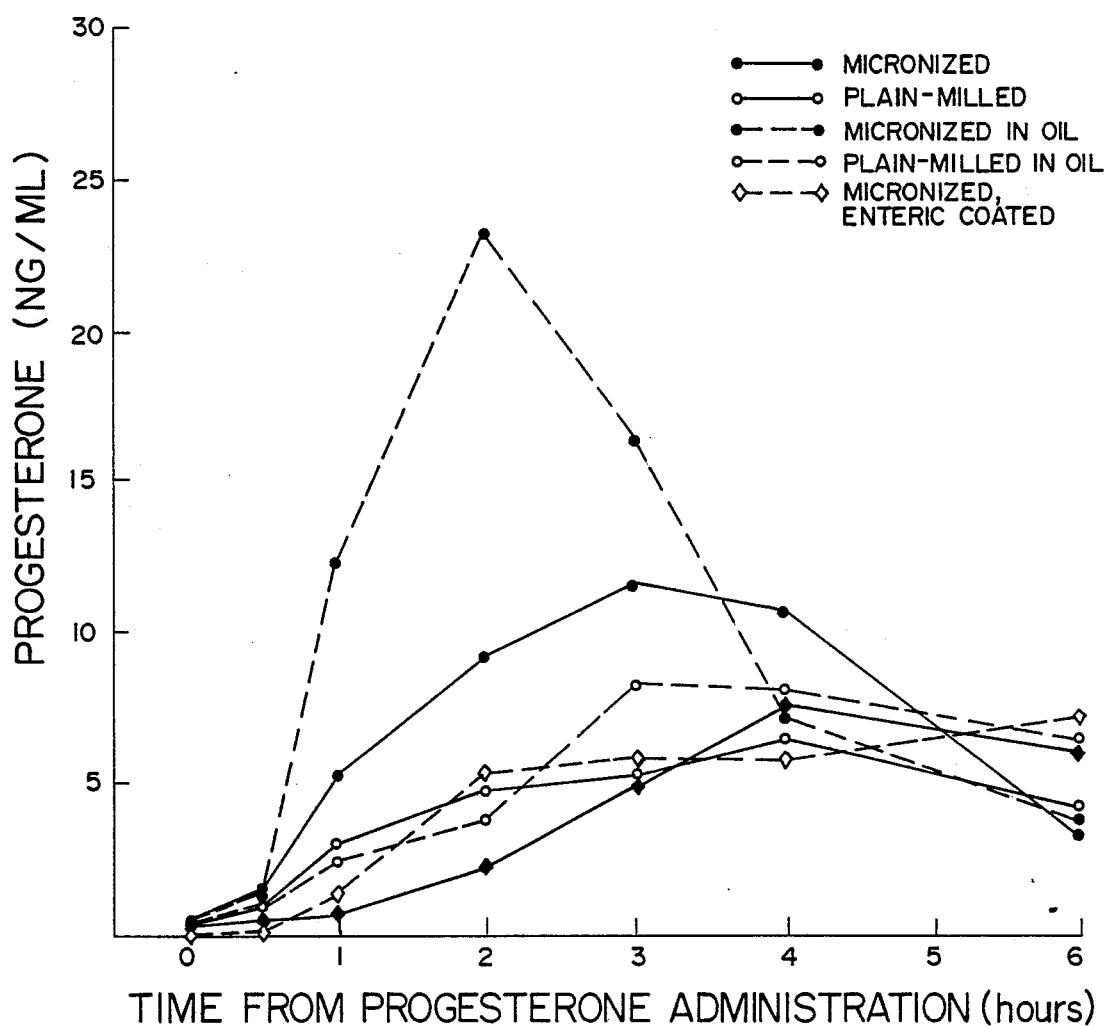
FIG. 1 is a graph which shows progerterone blood serum level, measured in nanograms per milliliter, versus time in hours, for several types of oral progesterone formulations.

The present invention provides a pharmaceutical formulation containing 17 beta-estradiol, progesterone and a highly unsaturated glyceride oil as essential ingredients. More particularly, 17 beta-estradiol is dissolved in the oil and the progesterone is incorporated in the oil as a suspension of micronized particles. The present invention is an improvement over the invention described in U.S. patent application Ser. No. 851,181, entitled "Pharmaceutical Composition Containing Progesterone" filed by Wayne S. Maxson, Joel D. Hargrove, and Philip G. Myers. The present invention further incorporates dissolved estradiol in the composition described in patent application Ser. No. 851,181. The specification of the above-reference application Ser. No. 851,181 is incorporated herein by reference.

The first ingredient of the invention is 17 beta-estradiol, which may be simply referred to herein as estradiol. The estradiol may be obtained from natural sources or may be produced synthetically. 17 beta-estradiol is commercially available as a microcrystalline (i.e. micronized) form. The micronized form is preferred because it dissolves more readily in the oil. However, it is not essential to use micronized estradiol since the composition of this invention uses it in a solubilized form. In fact, it is believed that the dissolution of estradiol in the oil enhances serum concentrations of this steroid to levels which are greater than those achieved by the "Estrace" micronized progesterone.

The second ingredient of the invention is micronized progesterone. Progesterone can be isolated from natural sources such as the corpus luteum of animals, or it may be produced synthetically. Progstrone is available commercially as USP Progesterone, or as micronized progesterone. The production of progesterone is described in U.S. Pat. No. 2,379,832, the specification of which is incorporated by reference herein.

The pharmaceutical composition according to the invention contains progesterone which has been micronized, i.e., the individual progesterone particles in the powder have been reduced in size to a few microns in diameter, or in the case of non-round particles, to a few microns in their largest dimension. As used herein, the term "micronized" progesterone or estradiol refers to a powdered progesterone or estradiol product wherein the particle size of virtually all (at least 99%) of the progesterone of estradiol particles is less than about 25 microns. The Besins patent cited above preferably employs micronized progesterone particles of which at least 80% of the particles have a particle size of from 5 to less than 15 microns. Besins teaches that micronized progesterone having a particle size of 5 microns or less looses a great part of its activity after being stored for three months (see Besins Table 3). By contrast, the pharmaceutical composition of the present invention can achieve excellent blood serum progesterone levels in humans, even after up to six months storage, using micronized progesterone having smaller size than the micronized particles preferred in the Besins patent.

Preferably, virtually all (99%) of the particles used in the present invention have particle sizes of less than 10 microns, and a majority (i.e. 78%) of these particles have particle sizes of less than 5 microns. Micronized progesterone products of this type are available from Berlichem, a division of Schering A. G., and the UpJohn Company. Micronized progesterone can be prepared from bulk progesterone in a radiator mill (jet air micronizer). The following U.S. patents disclose micronization techniques and machines, and are incorporated by reference herein:

Andrews, U.S. Pat. No. 4,189,102, issued Feb. 19, 1980;

Andrews, U.S. Pat. No. 4,018,388, issued Apr. 19, 1977;

Andrews, U.S. Pat. No. 2,032,827, issued Mar. 3, 1936.

The micronized progesterone products made by UpJohn and Berlichem can be used in the present invention without difficulty. In particular, the difficulties with hydroscopic and electrostatic properties of micronized progesterone described by Besins do not inhibit the practice of the present invention.

The second major component of the present invention is an oil which serves as a vehicle for the micronized progesterone and as a solvent for the estradiol. The composition and properties of the oil employed as the vehicle have a large effect on the effectiveness of the product. Oils high in glycerides of polynsaturated fatty acids are particularly effective for purposes of the present invention. Such polyunsaturated fatty acids include linoleic, linolenic, santalbic, eleosoteric, punicic, trichosanic, and parinaric acids. Of the foregoing acids, linoleic and linolenic acids are particularly common in certain natural vegatable oils. Accordingly, the oily vehicle according to the present invention is preferably a natural vegetable oil consisting mainly of glycerides of fatty acids, wherein the fatty acid glycerides comprise 51–95 wt. % of glycerides of polyunsaturated acids, particularly 70–80% of glycerides of polyunsaturated fatty acids. Such natural vegetable oils include, for example, safflower oil, linseed oil, soybean oil, corn oil, and sunflower oil. Mixtures of these and other vegetable oils having similar properties can also be employed.

The total unsaturated of an oil is indicated by its iodine value. The oil vehicle according to the present invention has an iodine value of at least 110, preferably 130–160, most preferably 140–150. The iodine values of the following oils are approximately as follows: safflower oil, 130–150; linseed oil, 175–190; soybean oil, 128–137; corn oil, 109–133; sunflower oil, 113–143. In contrast, peanut oil has a iodine value of 90–97.

Safflower oil has proven particularly effective as an oil vehicle for the pharmaceutical composition of this invention. The properties of safflower oil are as follows:

TABLE 1

PROPERTIES OF SAFFLOWER OIL

| | Broad Range | Preferred Range |
|---|---|---|
| Acid Value | 0.4–10 | 1.0–9.7 |
| Saponification Value | 186–194 | 188–194 |
| Iodine Value | 130–150 | 140–150 |
| Thiocyanogen Value | 82–87 | 82.5–86 |
| R-M(Reichert-Meissl) Value | less than 0.5 | 0.1–0.5 |
| Hydroxyl Value | 1–12 | 2.9–6.0 |
| Unsaponifiable (%) | less than 1.5 | 0.3–13 |
| Specific Gravity, 25/25° C. | 0.919–0.924 | 0.919–0.924 |
| Refractive Index, nD, 25° C. | 1.472–1.476 | 1.473–1.475 |
| Refractive Index, nD, 40° C. | 1.467–1.470 | 1.4690–1.4692 |
| Titer | 15–18 | 15–18 |

An edible oil having most or all of its properties in the foregoing ranges is particularly preferred for use in the present invention. The following Table gives approximate oil compositions of several typical vegetable oils:

TABLE 2

| Glycerides of Fatty Acids | OIL COMPOSITIONS (in wt. % of total glycerides) | | | |
|---|---|---|---|---|
| | Safflower | Linseed | Soybean | Peanut |
| Saturated (all kinds)* | 5–10 | 5.9–16 | 14–14.2 | 15.5–21.9 |
| Unsaturated | | | | |
| Oleic (1) | 13.4–21.1 | 13–28.6 | 22.9–26.1 | 42.3–71.5 |
| Linoleic (2) | 72.9–79 | 15.2–22.4 | 49.2–49.6 | 13.0–33.4 |
| Linolenic (3) | up to 0.13 | 47.3–54 | 7.9–10.7 | — |
| Others | — | up to 0.4 | — | 0.9–2.4 |

*Includes primarily palmitic, stearic, arachidic, behenic, lignoceric, and myristic acids. Typical breakdown for safflower oil: palmitic 6.4 wt. %, stearic 3.1 wt. %, arachidic 0.2 wt. %.
(1) Unsaturated with one double bond, 9-Octadecandic acid
(2) Unsaturated with double bonds, 9,12-Octadeadienoic acid
(3) Unsaturated with three double bonds, 9,13,15-Octadecatrienoic acid As Table 2 suggests, the oil used as the oily vehicle according to the present invention usually contains not more than 16 wt. % in glycerides of saturated fatty acids, particularly not more than about 10 wt. % in glycerides of saturated fatty acids.

The pharmaceutical composition of the present invention is particularly well suited for the filling of capsules. The oil dosage form can then be stored, preferably refrigerated, and prescribed and taken as needed. Soft gelatin capsules represent an inexpensive, convenient and orally digestable container for this pharmaceutical composition. The amount of estradiol and progesterone in a single capsule can vary widely and maintain effectiveness. However, in accordance with the nature of the capsules and the need of the patient, an estradiol dosage of 0.2–0.5 mg and a progesterone dosage of 50–100 mg per capsule is preferred. These doses have met with optimal serum concentrations of each steroid, atrophic endometrium on endometrium biopsy, maintenance of normal blood pressure and lipids and good clinical tolerance. The oil vehicle is used in an amount ranging from 1.5–2.5 milliliters of the oil per 1 gram of progesterone. Typically, 10,000 capsules of estradiol and micronized progesterone containing 0.35 mg and 100 mg of these steroids, respectively, can be prepared from 3.5 g of estradiol and 1,000 g of micronized progesterone in sufficient safflower oil to bring the total volume of suspension to 2900 ml.

The method of treating estrogen and progesterone deficiency after menopause varies. This generally involves the administration of an orally active, injectable or transdermal preparation of estrogen and an oral or injectable form of progestin. Clinical studies have demonstrated that the optimum dosage for the formulation of this invention is 3 capsules per day, with each capsule containing 0.3–0.4 mg of estradiol and 50 or 100 g of micronized progesterone.

A typical treatment plan according to the method of this invention is as follows: once menopause is documented and a breast examination and endometrial assessment show no evidence of malignancy, the capsules containing estradiol and micronized progesterone and oil can be administered at the above dose on a daily basis. Reassessment of breast and endometrium, as well as monitoring of blood studies such as serum cholesterol and HDL may be useful to monitor drug tolerance and the continued absence of side effects or development of malignancy. The dose can be adjusted based on symptoms which may relate to inadequate or excessive levels of either estradiol or progesterone.

The following examples illustrate various aspects of the invention. Example 1 shows the preparation of micronized progesterone used in the present invention. Example 2 illustrates the preparation of capsules containing 100 mg of suspended progesterone in safflower oil. Example 3 illustrates the preparation of capsules in accordance with this invention containing dissolved estradiol and suspended micronized progesterone in safflower oil. Example 4 compares the serum levels attained after administering 100 mg of various forms of progesterone. Example 5 illustrates the unexpected high serum levels obtained when estradiol is dissolved in a highly unsaturated oil (safflower oil) as compared to the serum levels achieved by adminstering micronized estradiol. Lastly, Example 6 demonstrates the efficiency and safety, especially the lack of side effects obtained when using the composition of this invention in the treatment of menopausal women.

EXAMPLE 1

Micronized progesterone was made according to the Berlichem method as follows: The jet air pulverizer used was a spiral-mill (fluid energy mill) manufactured by Schering, A. G. W. Germany. Milling occurs due to a strong continuous acceleration and deceleration of the feedstock by expanding nitrogen gas within the cylindrical milling chamber. Collisions occur constantly between the particles, resulting in comminution. A cyclone separator is used to internally classify the material. The finest particles leave the milling chamber through a central outlet, whereas the larger particles continue circling in the mainstream around the periphery. The fineness of the micronized material is controlled by adjusting the feed rate, milling gas pressure, and the angle of the gas jets. The charge rate of the mill is about 50 kg pergesterone per hour, and the air speed in the mill is about 300-500 meters per second. Due to the high air speed, the progesterone is in the mill for a period of time measured only in milliseconds or seconds, e.g., not more than about 10 seconds, depending on the particle size of the starting material (feed stock).

EXAMPLE 2

Berlichem micronized progesterone (200 g) consisting of 78% of particles having particle sizes less than 5 microns and 99% of particles having particle sizes of less than 10 microns, made according to the method described in Example 1, were mixed with 400 ml of safflower oil at room temperature. The resulting mixture was further mixed in an eyela D.C. stirrer DC-RT with a jacket heated to 24° C. for 15-30 minutes at a maximum rpm of 200. Upon completion of mixing, No. 3 plain gelatin capsules were filled using conventional capsule filling apparatus to prepare the oral dosage form of progesterone. Each capsule contained 100 mg of progesterone.

EXAMPLE 3

10,000 capsules of the formulation of the present invention were made by dissolving estradiol in safflower oil and then adding progesterone to the solution to form a suspension. To make 10,000 capsules of this combination, 3.5 g of estradiol and 100 g of micronized progesterone are needed for 10,000 No. 3 gelatin capsules. An aliquote of safflower oil is heated to 85°-88° C. While constantly stirring the oil, the total weight of estradiol is added and stirring is continued until complete dissolution and a crystal clear solution results. The estradiol solution is then allowed to come to room temperature and the progesterone is added while constantly stirring. Initially, approximately 700 ml of safflower oil is used. Additional safflower oil is added to bring the total volume of suspension to 2900 ml. When these ingredients have been thoroughly mixed, a smooth creamy white suspension results. 0.29 ml of the suspension is then placed into each No. 3 plain gelatin capsule and sealed. Each capsule contains 0.35 mg of estradiol and 100 mg of progesterone.

EXAMPLE 4

In this comparative example, various forms of orally adminsterable progesterone were prepared and their oral activity, as evidenced by serum levels, was compared to a formulation containing micronized progesterone suspended in safflower oil. Five forms of progesterone were compared: micronized progesterone, plan milled progesterone, micronized progesterone in safflower oil as described in Example 2, plain milled progesterone in safflower oil, and microcronized enteric coated progesterone.

The first form of progesterone listed above, i.e. "micronized progesterone" was not formulated with a vehicle. The plain milled progesterone formulations have a particle size of about 40 to about 50 microns. The enteric coating consists essentially of stearic acid and carnuba wax and ordinary vegetable cooking oil ("Crisco" oil made of partially hydrogenated soybean oil, "polysorbate 80", and polyglyerol esters).

Each human subject was given a 100 mg dose of one of the five formulations. Their blood serum level of progesterone was then tested after one-half hour, one hour, and hourly thereafter for a total of six hours. The results are graphically presented in FIG. 1. FIG. 1 demonstrates that the serum level curve for micronized progesterone in safflower oil is distinctly superior to the other forms of progesterone.

EXAMPLE 5

Figure 2:
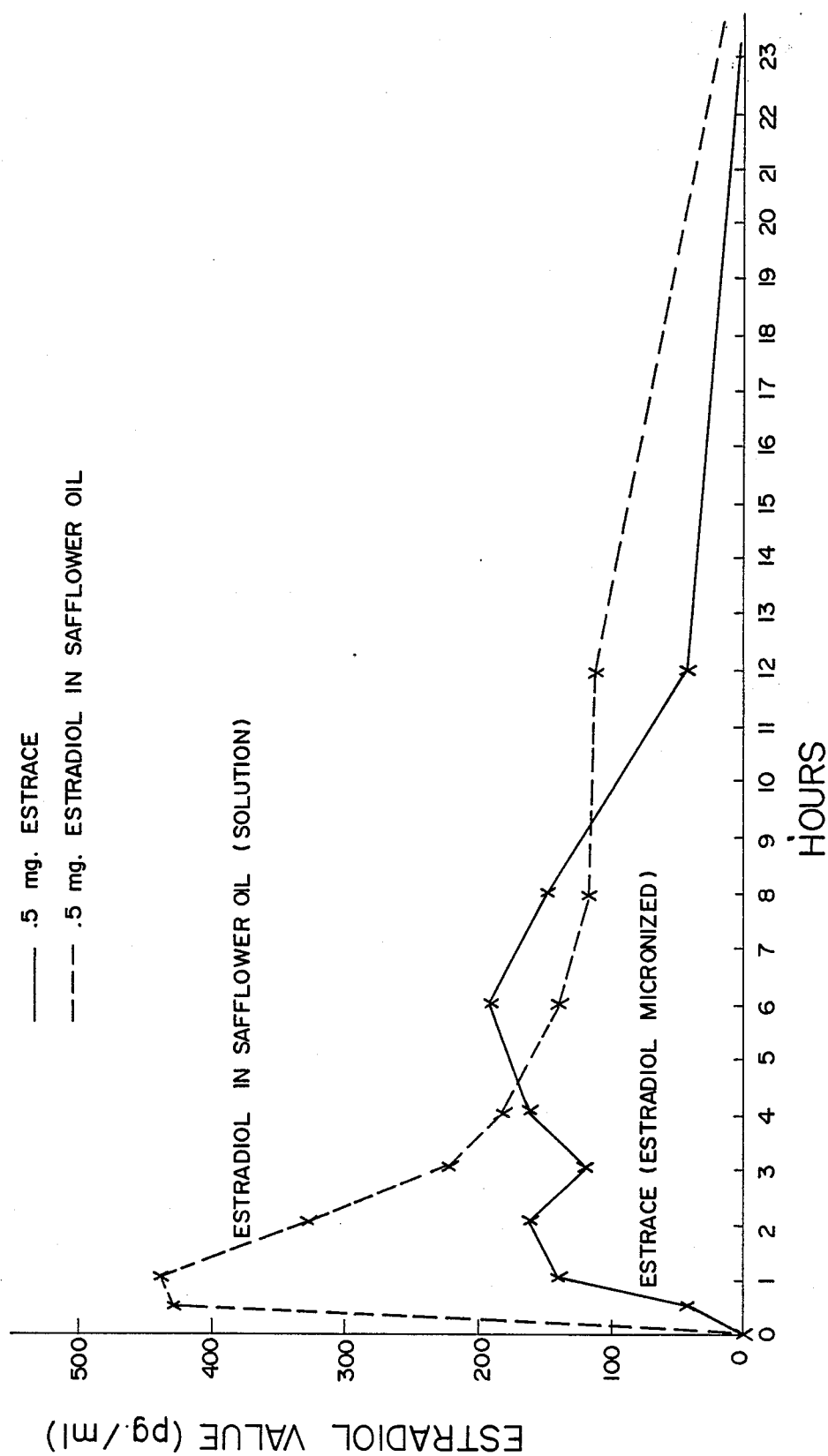
FIG. 2 is a graph which shows 17 beta-estrodiol blood serum level, measured in picograms per milliliter versus time in hours for micronized estradiol ("Estrace") and estradiol dissolved in safflower oil.

An absorption study was conducted for comparing serum levels of estradiol achieved after administering 0.5 mg micronized estradiol as currently available from Mead-Johnson as "Estrace" and a preparation containing 0.5 mg micronized estradiol which has been dissolved in safflower oil. Each volunteer was given 0.5 mg of one of the two formulations. The blood serum levels were then evaluated on an hourly basis for 24 hours. The results are illustrated in the graph of FIG. 2. The results clearly demonostrate that enhanced serum levels are achieved when the estradiol is dissolved in the unsaturated oil. This result is unexpected given the prior art preference for micronized forms of estradiol.

FIG. 2 also shows that both preparations resulted in a decline in serum estrogen concentration after 12 hours. Consequently, a twice a day dose is preferably for the maintenance of physiologic estrogen serum concentrations. When three capsules are given daily, a patient may conveniently take one in the morning and two before bedtime.

EXAMPLE 6

A clinical study was performed to evaluate a continuous daily hormone replacement program using estradiol and progesterone in accordance with this invention. The study included the safety and effectiveness of the present invention in relieving menopausal symptoms. The study also included a determination of the efficacy of the present invention in eliminating uterine bleeding. The study also evaluated the acceptability of the present invention.

The clinical study utilized capsules made in accordance with Example 3. Thus, each capsule contained 0.35 mg of micronized estradiol dissolved in safflower oil and 100 mg of micronized progesterone suspended in the estradiol-oil solution.

The drug was given on a twice daily dosage schedule for 12 months. Patients were seen at the beginning of the study (control) and at 1, 3, 6, and 12 months. Relief of symptoms and side effects were evaluated by questionaire and interview. Safety was checked by physical examination, CBC, urinalysis, CMA-12, lipids, endocrine studies, endometrial biopsies, and mammogram.

Eleven symptomatic perimenopausal and postmenopausal women volunteered to participate in the study. All had an intact uterus, and none had any chronic diseases. Each volunteer had menopausal symptoms.

The protocol for the clinical study is summarized in Table 3.

TABLE 3

| PROTOCOL | CONTROL | MONTH 1 | 3 | 6 | 12 |
|---|---|---|---|---|---|
| Drug given twice daily for 12 months | X | X | X | X | X |
| Symptom questionnaire and interview | X | X | X | X | X |
| Physical examination | X | X | X | X | X |
| Endocrine Studies | X | X | X | X | X |
| Endometrial Biopsy | X | X | X | X | X |
| CBC, SMA-12, lipids, urinalysis | X | X | X | X | X |
| Mammogram | X | | | | X |
| Transvaginal ultrasound endometrium | | | | | X |

One patient dropped from the study during the first month because she experienced annoying drowsiness and dizziness shortly after taking each dose of medication. Ten patients remained for the duration of the study.

Figure 3:
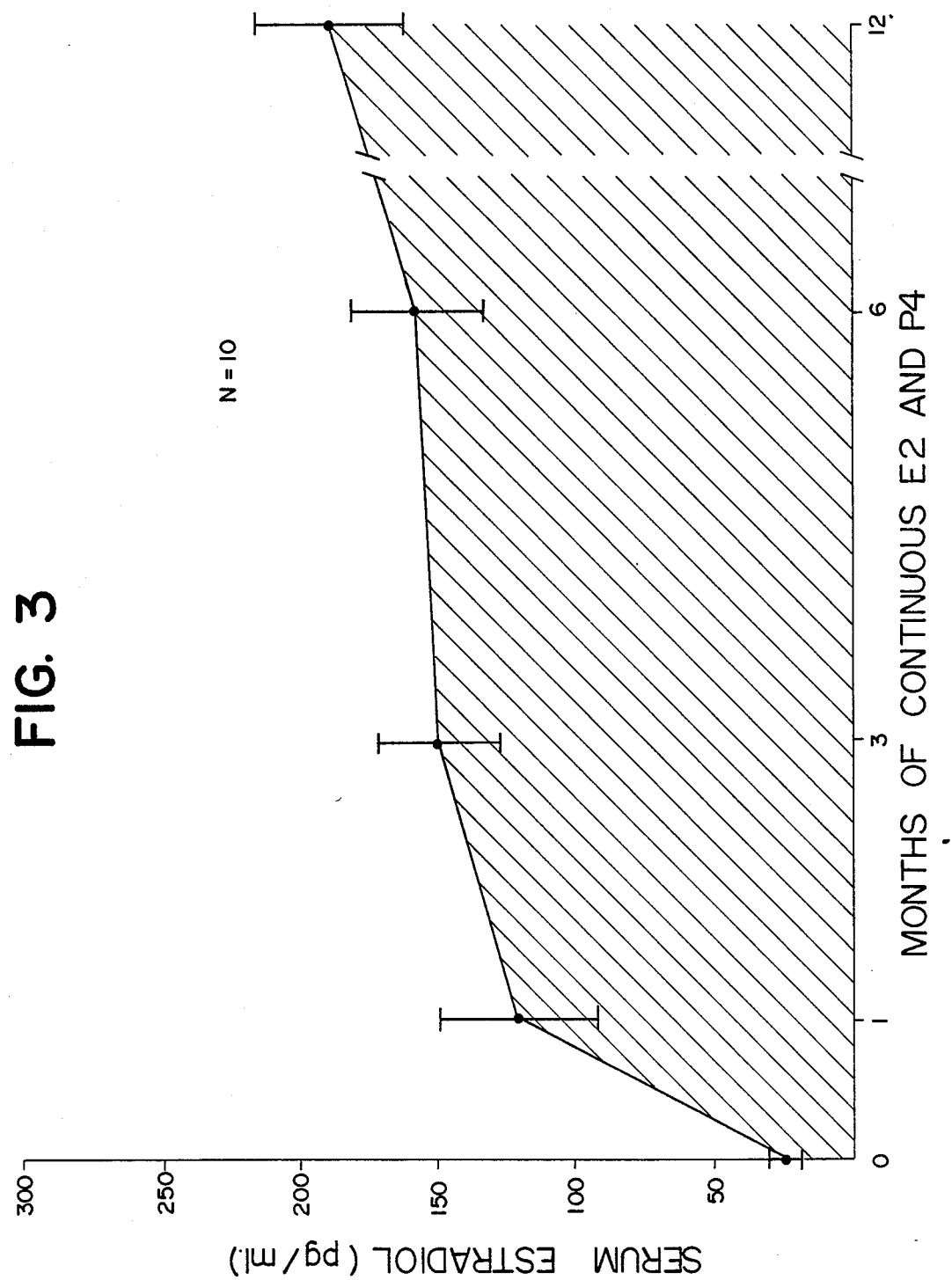
FIG. 3 is a graph which shows serum estradiol levels measured in picograms per milliliter versus months of continuous therapy with the formulation of this invention containing estradiol and progesterone in an unsaturated oil.

During the study, the blood levels of the hormones were assessed at the intervals shown in the protocol. The estradiol levels are shown in FIG. 3. It is apparent from FIG. 3 that estradiol was significantly elevated from base line to levels typically seen in the luteral phase of a normal menstrual cycle.

Figure 4:
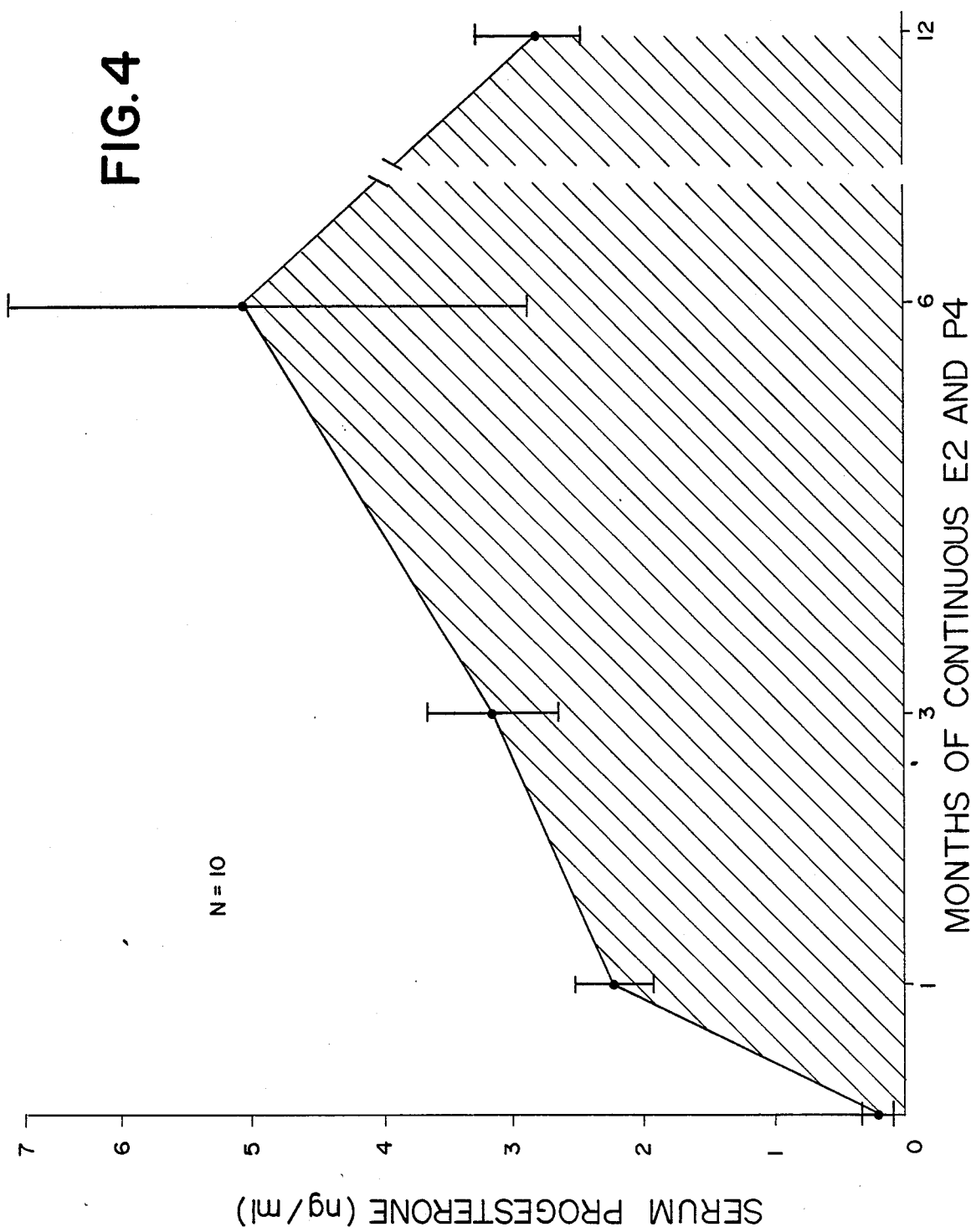
FIG. 4 is a graph which shows serum progesterone measured in nanograms per milliliter versus months of continuous therapy with the formulation of this invention containing estradiol and progesterone in an unsaturated oil.

FIG. 4 shows the blood serum progesterone levels of the patients taken at the points of time indicated by the protocol. It is apparent from FIG. 4 that the progesterone level was also significantly elevated from base line and remained there throughout the period of observation.

Figure 5:
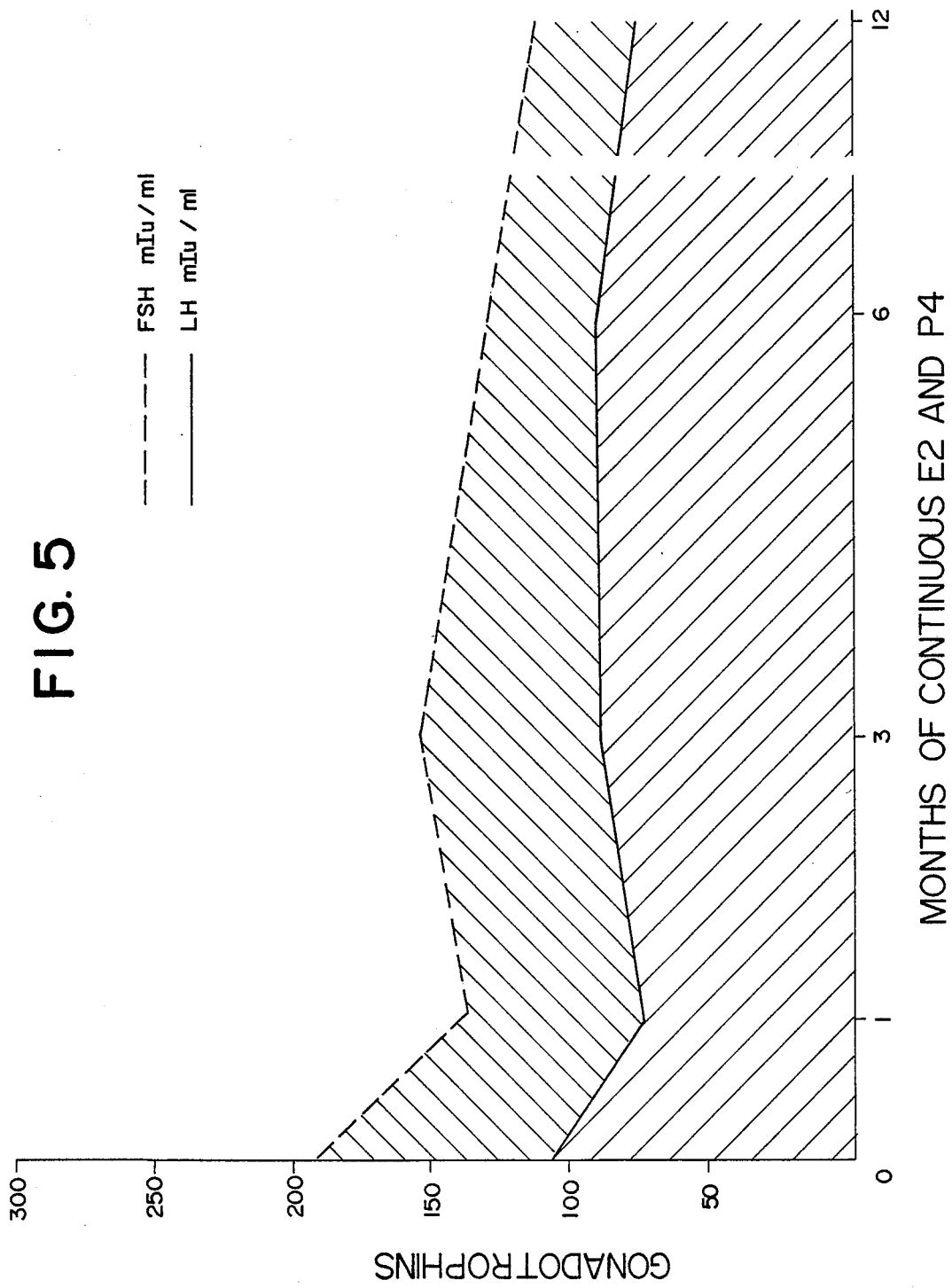
FIG. 5 is a graph which shows the level of gonadotropins (FSH and LH) versus months of continuous therapy with the formulations of this invention containing estradiol and progesteone in an unsaturated oil.

The gonadotrophins were similarly measured throughout the study at the time intervals indicated in the protocol. The results are summarized in FIG. 5. It is apparent from FIG. 5 that the gonadotrophins decreased. However, they remained in the post-menopausal range throughout the study.

It was observed throughout the study that the menopausal symptoms were effectively relieved. Anxiety, although not necessarily related to menopause, was relieved in half of those with this symptom. Depression, again not necessarily a menopausal symptom, was not relieved in a single patient with this symptom. The symptoms of the patients at the beginning and at the end of the 12 month period are summarized in Table 4 below:

TABLE 4

| EFFECT ON SYMPTOMS (N = 10) | | |
|---|---|---|
| Symptom | Control Month | 12 Months |
| Hot flashes | 9 | 0 |
| Night Sweats | 6 | 0 |
| Insomnia | 4 | 1 |
| Decreased Libido | 6 | 0 |
| Dyspareunia or vaginal dryness | 5 | 0 |
| Anxiety | 6 | 3 |
| Depression | 1 | 1 |

Figure 6:
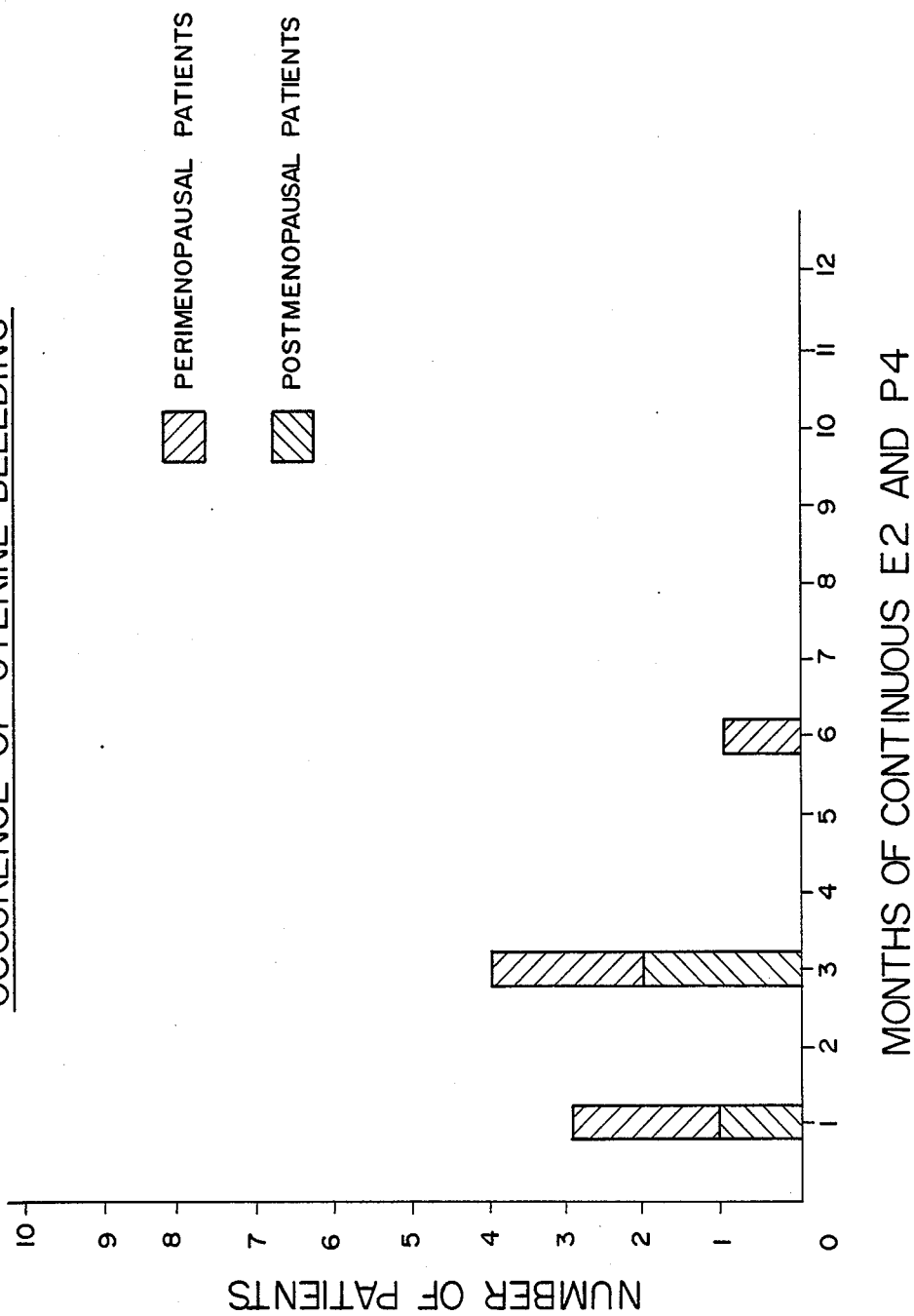
FIG. 6 is a bar graph which shows the number of patients having uterine bleeding versus the number of months of continuous therapy with the formulation of this invention containing estradiol and progesterone in an unsaturated oil.

During the study there were eight episodes of uterine bleeding. Seven occurred during the first three months. One of the perimenopausal subjects has a period at six months. There were no bleeding episodes beyond six months. The data obtained in connection with the occurrence of uterine bleeding is shown in FIG. 6.

Examination of the patients during the study shows that, with the exception of a decrease in cholesterol, there was no change in the SMA-12, CBC, blood pressure and mammogram.

Figure 7:
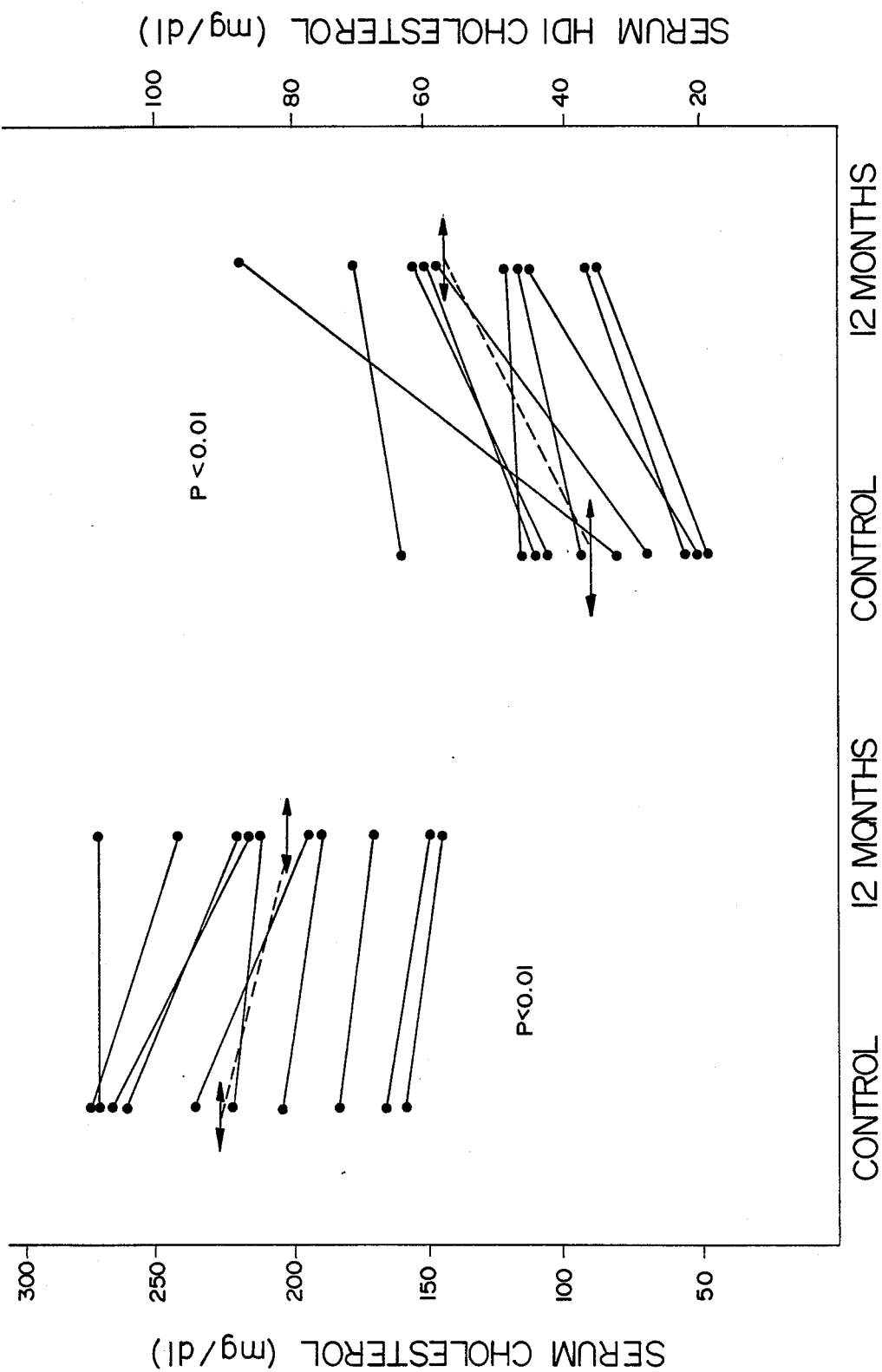
FIG. 7 is a graph which shows serum cholesterol and serum HDL cholesterol levels at the beginning of therapy and after 12 months of continuous therapy with the formulation of this invention containing estradiol and progesterone in an unsaturated oil.

It was also observed during this study that all patients experienced a decrease in serum cholesterol and all patients experienced an increase in HDL-cholesterol. This data is illustrated in FIG. 7.

Endometrial biopsies by the end of the study yielded only a very scanty amount of tissue that on histologic study showed only blood, mucus, and scattered fragments of atrophic stroma and epithelial elements.

Transvaginal ultrasonography done at the completion of the study was consistent with an thin atrophic endometrium.

By the end of 12 months, the hormone therapy was effective in all patients in producing a quiescent, atrophic endometrium. The uterine bleeding episodes did not correlate with the endometrial histology.

The endometrial histology and uterine bleeding data taken during the experiment is summarized in Table 5:

TABLE 5

| N = 10 | ENDOMETRIAL HISTOLOGY | | | UTERINE |
|---|---|---|---|---|
| Month | Proliferative | Secretory | Quiescent | BLEEDING |
| 0 | | 1 | 9 | 3 |
| 1 | | 2 | 8 | 0 |
| 3 | 1 | | 9 | 4 |
| 6 | | 1 | 9 | 1 |
| 12 | | | 10 | 0 |

As a result of this study, it has been concluded that the hormone treatment was efficaceous in relieving menopausal symptoms. It was effective in eliminating uterine bleeding. There was no evidence of endometrial stimulation on frequent endometrial biopsies. It produced a beneficial effect on serum cholesterol and HDL-cholesterol. There was no untoward effect on the breasts or liver. It was well tolerated without significant side effects or complications. Its acceptability by the patients was further attested by all patients requesting to continue the drug at completion of the study.

While the present invention has been described in terms of certain preferred embodiments and exemplified with respect thereto, one skilled in the art will readily appreciate that various modifications, changes, omissions and substitutions may be made without departing from the spirit thereof. It is intended, therefore, that the present invention be limited solely by the scope of the following claims.

I claim:

1. A pharmaceutical composition for treating menopausal symptoms in women which comprises estradiol dissolved in a highly unsaturated edible oil containing a suspension of micronized progesterone particles; said oil comprising glycerides of one or more polyunsaturated fatty acids; said estradiol and progesterone being present in a therapeutically effective amount for treating menopause; and said estradiol and progesterone being present in an amount so that the composition can be orally administered to provide a daily dosage rate of 0.9–1.2 mg. estradiol and 150–300 mg. progesterone.

2. The composition of claim 1, wherein at least 51% of the glycerides are glycerides of polyunsaturated fatty acids.

3. The composition of claim 2, wherein said oil has an acid value in the range of 0.4–10, a saponification value in the range of 186–194, an iodine value in the range of 130–150, a thiocyanogen value in the range of 82–87, a R-M value of less than 0.5, an hydroxyl value in the range of 1–12, an unsaponifiable content of less than 1.5 wt.%, and a specific gravity in the range of 0.919–0.924.

4. The pharmaceutical composition of claim 1, wherein the oil consists essentially of glycerides having 5–10 wt.% saturated fatty acids; 13–22 wt.% oleic acid, and 72–79 wt.% linoleic acid.

5. The composition of claim 1, wherein the oil is selected from the group consisting of safflower oil, linseed oil, soybean oil, corn oil, sunflower oil, and mixtures thereof.

6. The composition of claim 4, wherein the oil is safflower oil.

7. A pharmaceutical composition which comprises estradiol dissolved in a edible glyceride oil and micronized progesterone particles suspended in the oil; said oil having an iodine value of at least 110 and comprising glycerides of one or more polyunsaturated fatty acids; and said progesterone particles being of a particle size wherein at least 99% of the particles are less than 10 microns in diameter and at least 78% of the particles are less than 5 microns in diameter; said estradiol and progesterone being present in a therapeutically effective amount for treating menopause; and said estradiol and progesterone being present in an amount so that the composition can be orally administered to provide a daily dosage rate of 0.9–1.2 mg. estradiol and 150–300 mg. progesterone.

8. The composition of claim 7, wherein the oil has an iodine value of 130–160.

9. The composition of claim 8, wherein the oil has an iodine value of 140–150.

10. The composition of claim 7, wherein the oil has an acid value in the range of 0.4–10, a saponification value in the range of 186–194, an iodone value in the range of 130–150, a thiocyanogen value in the range of 82–87, and R-M value of less than 0.5, a hydroxyl value in the range of 1–12, an unsaponifiable content of less than 1.5 wt.%, and a specific gravity in the range of 0.919–0.924.

11. The composition of claim 7, wherein the oil consists of glycerides having 5–10 wt.% saturated fatty acids; 13–22 wt.% oleic acid, and 72–79 wt.% linoleic acid.

12. The composition of claim 7, wherein the oil is selected from the group consisting of safflower oil, linseed oil, soybean oil, corn oil, sunflower oil, and mixtures thereof.

13. The composition of claim 12, wherein the oil is safflower oil.

14. A capsule for oral administration of estradiol and progesterone which comprises a pharmaceutically acceptable capsule containing estradiol dissolved in a highly unsaturated edible oil containing a suspension of micronized progesterone particles therein; said oil comprising glycerides of one or more polyunsaturated acids; said capsule containing estradiol and progesterone in a therapeutically effective amount for treating menopause; and said capsule containing estradiol and progesterone in an amount so that the capsules can be orally administered to provide a daily dosage rate of 0.9–1.2 mg. estradiol and 150–300 mg. progesterone.

15. The capsule of claim 14, wherein the oil has an iodine value of at least 110.

16. The capsule of claim 15, wherein the progesterone particles are of a particle size wherein 99% of the particles are less than 10 microns in diameter and at least 78% of the particles are less than 5 microns in diameter.

17. The capsule of claim 16, wherein the oil is selected from the group consisting of safflower oil, linseed oil, soybean oil, corn oil, sunflower oil, and mixtures thereof.

18. The capsule of claim 17, wherein the oil is safflower oil.

19. The capsule of claim 14, which contains 0.2–0.5 mg. estradiol and 50–100 mg. progesterone.

20. The capsule of claim 14, which contains 0.2–0.5 mg. estradiol and 50–100 mg. progesterone.

21. The capsule of claim 19, which contains 0.35 mg. estradiol and 100 mg. progesterone.

22. A method for treating menopausal symptoms in women which comprises orally administering to a woman suffering from menopausal symptoms a therapeutically effective amount of a pharmaceutical composition which comprises estradiol dissolved in a highly unsaturated oil containing a suspension of micronized progesterone particles; said oil comprising glycerides of one or more polyunsaturated fatty acids; said composition containing estradiol and progesterone in a therapeutically effective amount for treating menopause; and said composition being orally administered in an amount to provide a daily dosage rate of 0.9–1.2 mg. estradiol and 150–300 mg. progesterone.

23. The method of claim 21, wherein the progesterone particles are of a particle size wherein 99% of the particles are less than 10 microns in diameter and at least 78% of the particles are less than 5 microns in diameter.

24. The method of claim 23, wherein the composition is contained in a digestible capsule.

25. The method of claim 23, wherein the daily dosage rate is adminstered in the form of capsules containing 0.2–0.5 mg. estradiol and 50–100 mg. progesterone.

26. The capsule of claim 25, wherein the oil is selected from the group consisting of safflower oil, linseed oil, soybean oil, corn oil, sunflower oil, and mixtures thereof.

27. The method of claim 26, wherein the capsule contains 0.35 mg. estradiol and 100 mg. progesterone.

28. The method of claim 27, wherein the oil is safflower oil.

29. The method of increasing blood serum estradiol and progesterone levels in humans which comprises orally administering to humans to composition comprising estradiol dissolved in an edible oil containing a suspension of micronized progesterone particles, said oil comprising glycerides of one or more polyunsaturated fatty acids.

30. The method of claim 29, wherein the oil has an iodine value of at least 110 and the progesterone particles are of a particle size wherein 99% of the particles are less than 10 microns in diameter and at least 78% of the particles are less than 5 microns in diameter.

31. The method of claim 30, wherein the oil is selected from the group consisting of safflower oil, linseed oil, soybean oil, corn oil, sunflower oil, and mixtures thereof.

32. The method of claim 31, wherein the oil is safflower oil and the estradiol, progesterone and oil containing composition is contained in a digestible capsule.

33. A method for preparing an orally active pharmaceutical composition comprising estradiol, progesterone and a glyceride oil of one or more polyunsaturated acids, which method comprises the steps of: heating a quantity of the oil; dissolving a quantity of estradiol in the oil to form a solution; cooling the solution to room temperature; stirring and mixing micronized progesterone into the solution, whereby a composition is formed containing estradiol dissolved in the oil which contains suspended micronized particles of progesterone and solubilized progesterone.

34. The method of claim 33, wherein the mixture formed in claim 33 is further diluted with additional quantities of oil.

* * * * *